(12) United States Patent
Koseoglu et al.

(10) Patent No.: US 11,066,344 B2
(45) Date of Patent: *Jul. 20, 2021

(54) METHODS AND SYSTEMS OF UPGRADING HEAVY AROMATICS STREAM TO PETROCHEMICAL FEEDSTOCK

(71) Applicant: Saudi Arabian Oil Company, Dhahran (SA)

(72) Inventors: Omer Refa Koseoglu, Dhahran (SA); Robert Peter Hodgkins, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/879,212

(22) Filed: May 20, 2020

(65) Prior Publication Data

US 2020/0283355 A1    Sep. 10, 2020

Related U.S. Application Data

(60) Continuation-in-part of application No. 16/600,285, filed on Oct. 11, 2019, now Pat. No. 10,759,723, which is a division of application No. 16/388,563, filed on Apr. 18, 2019, now Pat. No. 10,508,066, which is a continuation-in-part of application No. 16/032,642, filed on Jul. 11, 2018, now Pat. No. 10,294,172, which is a continuation of application No. 15/435,039, filed on Feb. 16, 2017, now Pat. No. 10,053,401.

(51) Int. Cl.
C07C 4/24        (2006.01)
C07C 6/12        (2006.01)
C07C 4/26        (2006.01)

(52) U.S. Cl.
CPC ............... *C07C 4/24* (2013.01); *C07C 4/26* (2013.01); *C07C 6/126* (2013.01); *C07C 2529/16* (2013.01)

(58) Field of Classification Search
CPC .... C07C 4/24; C07C 4/26; C07C 4/18; C07C 6/126
See application file for complete search history.

(56) References Cited

U.S. PATENT DOCUMENTS

| | | |
|---|---|---|
| 2,697,684 A | 12/1954 | Hemminger et al. |
| 2,836,632 A | 5/1958 | Fetterly |
| 2,881,226 A | 4/1959 | Wadsworth |

(Continued)

FOREIGN PATENT DOCUMENTS

| | | |
|---|---|---|
| CN | 101376823 A | 3/2009 |
| CN | 102037102 A | 4/2011 |

(Continued)

OTHER PUBLICATIONS

Buchanan, et al. "Acid-Catalyzed Cracking of Surface-Immobilized 1, 3-Diphenylpropane in Dispersed Solids." Abstracts of Papers of the American Chemical Society. vol. 201. 1155 16th St, Nw, Washington, Dc 20036: Amer Chemical Soc, 1991.

(Continued)

*Primary Examiner* — Lessanework Seifu
(74) *Attorney, Agent, or Firm* — Bracewell LLP; Constance G. Rhebergen; Kevin R. Tamm

(57) ABSTRACT

Provided here are systems and methods that integrate a hydrodearylation process and a transalkylation process into an aromatic recovery complex. Various other embodiments may be disclosed and claimed.

23 Claims, 4 Drawing Sheets

(56) References Cited

U.S. PATENT DOCUMENTS

| | | |
|---|---|---|
| 2,885,452 A | 5/1959 | Schmerling |
| 2,954,413 A | 9/1960 | Kroeper |
| 3,053,760 A | 9/1962 | Henke |
| 3,062,903 A | 11/1962 | Odioso |
| 3,067,128 A | 12/1962 | Kimberlin, Jr. |
| 3,075,022 A | 1/1963 | Gammon |
| 3,116,345 A | 12/1963 | Slaymaker |
| 3,145,238 A | 8/1964 | Kestner |
| 3,159,565 A | 12/1964 | Kimberlin et al. |
| 3,204,007 A | 8/1965 | Mukai |
| 3,252,888 A | 5/1966 | Langer, Jr. |
| 3,373,217 A | 3/1968 | Engelbrecht et al. |
| 3,441,625 A | 4/1969 | Bargeron |
| 3,485,883 A | 12/1969 | Engelbrecht et al. |
| 3,557,234 A | 1/1971 | Henry |
| 3,557,235 A | 1/1971 | Henry |
| 3,595,933 A | 7/1971 | Feldman |
| 3,624,172 A | 11/1971 | Adams |
| 3,649,520 A | 3/1972 | Graven |
| 3,702,292 A | 11/1972 | Burich |
| 3,723,256 A | 3/1973 | Thompson |
| 3,795,608 A | 3/1974 | Fujiyama |
| 3,933,619 A | 1/1976 | Kozlowski |
| 3,939,221 A | 2/1976 | Pearce |
| 3,957,621 A | 5/1976 | Bonacci et al. |
| 4,031,154 A | 6/1977 | Edison et al. |
| 4,070,408 A | 1/1978 | Vickers |
| 4,192,961 A | 3/1980 | Gankin |
| 4,203,826 A | 5/1980 | Mayes |
| 4,222,854 A | 9/1980 | Vorhis, Jr. et al. |
| 4,242,531 A | 12/1980 | Carter |
| 4,244,808 A | 1/1981 | Lang et al. |
| 4,324,935 A | 4/1982 | Wernicke |
| 4,532,370 A | 7/1985 | Le Quan |
| 4,538,018 A | 8/1985 | Carter |
| 4,747,933 A | 5/1988 | Hibbs |
| 4,806,700 A | 2/1989 | Martindale |
| 4,923,589 A | 5/1990 | Dalson |
| 5,877,385 A | 3/1999 | Lee |
| 6,281,398 B1 | 8/2001 | Belloir et al. |
| 6,375,802 B1 | 4/2002 | Gentry |
| 6,398,947 B2 | 6/2002 | Beck |
| 6,565,742 B1 | 5/2003 | Gentry |
| 6,616,831 B1 | 9/2003 | Gentry |
| 6,787,025 B2 | 9/2004 | Mukherjee et al. |
| 6,793,804 B1 | 9/2004 | Lindsay et al. |
| 7,507,325 B2 | 3/2009 | Gueret et al. |
| 7,723,554 B2 | 5/2010 | Arca |
| 7,880,045 B2 | 2/2011 | Arca |
| 7,964,763 B2 | 6/2011 | Dixon et al. |
| 8,168,844 B2 | 5/2012 | Arca |
| 8,536,397 B2 | 9/2013 | Noll |
| 8,932,451 B2 | 1/2015 | Strauss et al. |
| 8,975,462 B2 | 3/2015 | Kim |
| 9,090,521 B2 | 7/2015 | Al-Haji |
| 9,109,169 B2 | 8/2015 | Al-Therwi |
| 9,221,729 B1 | 12/2015 | Lee |
| 9,909,075 B2 | 3/2018 | Klein et al. |
| 10,006,821 B1 | 6/2018 | Boger |
| 10,053,401 B1 | 8/2018 | Beadle et al. |
| 10,093,873 B2 | 10/2018 | Koseoglu et al. |
| 10,294,172 B2 | 5/2019 | Beadle et al. |
| 10,508,066 B2 | 12/2019 | Koseoglu et al. |
| 2001/0001448 A1 | 5/2001 | Kapoor |
| 2013/0144097 A1 | 6/2013 | Bender |
| 2013/0345486 A1 | 12/2013 | Noll |
| 2015/0166435 A1 | 6/2015 | Serban et al. |
| 2015/0251973 A1 | 9/2015 | Tinger |
| 2015/0299069 A1 | 10/2015 | Azam |
| 2015/0299086 A1 | 10/2015 | Farha |
| 2016/0045841 A1 | 2/2016 | Kaplan |
| 2019/0241486 A1 | 8/2019 | Koseoglu et al. |
| 2020/0039898 A1 | 2/2020 | Koseoglu et al. |

FOREIGN PATENT DOCUMENTS

| | | |
|---|---|---|
| CN | 103121895 B | 6/2015 |
| EP | 0284228 B1 | 1/1992 |
| EP | 2773602 B1 | 7/2017 |
| EP | 3539651 A1 | 9/2019 |
| FR | 2768724 A1 | 3/1999 |
| GB | 1279218 A | 6/1972 |
| GB | 1404776 A | 9/1975 |
| GB | 2034351 A | 6/1980 |
| JP | 3639243 B2 | 4/2005 |
| WO | 9617039 A1 | 6/1996 |
| WO | 9923192 A1 | 5/1999 |
| WO | 2018127812 A1 | 7/2018 |
| WO | 2018152389 A1 | 8/2018 |

OTHER PUBLICATIONS

Coco et al., "Multidimensional gas chromatographic determination of paraffins, olefins and aromatics in naphthas", Annali Di Chimica, EUCHEM 2006 Conference, Rimini Italy, 2006, p. 1.

Commereuc, D., et al. "Dimerize ethylene to butene-1." Hydrocarbon processing 63.11 (1984): 118-120.

International Search Report and the Written Opinion of the International Searching Authority dated Nov. 28, 2013; International Application No. PCT/US2013/039191; International File Date: May 2, 2012.

International Search Report and Written Opinion dated Apr. 19, 2018 for corresponding PCT/US2018/018471.

International Search Report and Written Opinion for related PCT application PCT/US2017/047842 dated Oct. 11, 2017.

Partial International Search Report of the International Searching Authority, dated Jul. 4, 2013; International Application No. PCT/US2013/039191; International File Date: May 2, 2013.

Farrell, L. M., "Developments in LAO Comonomer Technologies for Polyethylene"; PERP 2011S11 Report; May 2012, pp. 1-7.

Hennico, A., et al. "Butene-1 is made from ethylene." Hydrocarbon Processing;(USA) 69.3 (1990).

Hu et al., "Molecular modeling and optimization for catalytic reforming", Chemical Engineering Communications, 2004, p. 1.

Liu et al., "A scenario-based clean gasoline production strategy for china national petroleum corporation", Petroleum Science, 2008, p. 1.

Nafis et al., "Recovering Intermediate-Range FCC Naphtha", Handbook of Petroleum Refining Processes Third Edition, 2004, pp. 11.72-11.78, McGraw Hill, USA.

Smith, P. D., et al. "Ethylene Dimerization over Supported Titanium Alkoxides", Journal of Catalysis 105, pp. 187-198, 1987.

Smolin, E. M., et al. "Preparation of Substituted Styrenes by Cracking of Diarylethanes." Industrial & Engineering Chemistry Product Research and Development 3.1 (1964): 16-19.

U.S. Appl. No. 16/424,273, "Systems and Processes for Suppressing Heavy Polynuclear Aromatic Deposition in a Hydrocracking Process", filed May 28, 2019.

U.S. Appl. No. 16/592,591, "Two Stage Hydrodearylation Systems and Processes to Convert Heavy Aromatics Into Gasoline Blending Components and Chemical Grade Aromatics", filed Oct. 10, 2019.

U.S. Appl. No. 16/594,768, "Catalytic Hydrodearylation of Heavy Aromatic Stream Containing Dissolved Hydrogen", filed Oct. 7, 2019.

U.S. Appl. No. 16/600,055, "Systems and Processes to Deolefinate Aromatic-Rich Hydrocarbon Streams", filed Oct. 11, 2019.

U.S. Appl. No. 16/600,285, "Methods and Systems of Upgrading Heavy Aromatics Stream to Petrochemical Feedstock", filed Oct. 11, 2019.

U.S. Appl. No. 16/672,052, "Methods and Systems of Upgrading Heavy Aromatics Stream to Petrochemical Feedstock", filed Nov. 1, 2019.

U.S. Appl. No. 16/672,254, "Integrated Methods and Systems of Hydrodearylation and Hydrodealkylation of Heavy Aromatics to Produce Benzene, Toluene, and Xylenes", filed Nov. 1, 2019.

(56) References Cited

OTHER PUBLICATIONS

Viswanadham et al., "Reformulation of FCC gasoline" Fuel, Mexican Congress on Chemical Reaction Engineering, Mexico City, Mexico Inst. Mexicano Petroleo, Jun. 2007, p. 1.
Wei, Xian-Yong, et al. "FeS2-Catalyzed Hydrocracking of. a.OMEGA.-Diarylalkanes." Bulletin of the Chemical Society of Japan 65.4 (1992): 1114-1119.
International Search Report and Written Opinion for related PCT application PCT/US2020/028614 dated Jul. 15, 2020.
International Search Report and Written Opinion for related PCT application PCT/US2020/058042, dated Feb. 10, 2021.

METHODS AND SYSTEMS OF UPGRADING HEAVY AROMATICS STREAM TO PETROCHEMICAL FEEDSTOCK

CROSS-REFERENCE TO RELATED APPLICATIONS

This application is a continuation-in-part application of U.S. application Ser. No. 16/600,285, filed Oct. 11, 2019, which itself is a divisional application of U.S. application Ser. No. 16/388,563, filed Apr. 18, 2019 and issued as U.S. Pat. No. 10,508,066 on Dec. 17, 2019, which itself is a continuation-in-part application of U.S. application Ser. No. 16/032,642, filed on Jul. 11, 2018 and issued as U.S. Pat. No. 10,294,172 on May 21, 2019, which is a continuation application of U.S. application Ser. No. 15/435,039, filed on Feb. 16, 2017 and issued as U.S. Pat. No. 10,053,401 on Aug. 21, 2018.

TECHNICAL FIELD

The disclosure relates to methods and systems of upgrading heavy aromatics stream to petrochemical feedstock, and more specifically to a combination of a hydrodearylation unit and a transalkylation unit in an aromatics recovery complex.

BACKGROUND

In an aromatics complex, a variety of process units are used to convert naphtha or pyrolysis gasoline into benzene, toluene and mixed xylenes, which are basic petrochemical intermediates used for the production of various other chemical products. In order to maximize the production of benzene, toluene and mixed xylenes, the feed to an aromatics complex is generally limited from $C_6$ up to $C_{11}$ compounds. In most aromatic complexes, the mixed xylenes are processed within the complex to produce the particular isomer-para-xylene, which can be processed downstream to produce terephthalic acid. This terephthalic acid is used to make polyesters, such as polyethylene terephthalate. In order to increase the production of benzene and para-xylene, the toluene and $C_9$ and $C_{10}$ aromatics are processed within the complex through a toluene, $C_9$, $C_{10}$ transalkylation/toluene disproportionation (TA/TDP) process unit to produce benzene and xylenes. Any remaining toluene, $C_9$, and $C_{10}$ aromatics are recycled to extinction. Compounds heavier than $C_{10}$ are generally not processed in the TA/TDP unit, as they tend to cause rapid deactivation of the catalysts used at the higher temperatures used in these units, often greater than 400° C.

When para-xylene is recovered from mixed xylenes by a selective adsorption process unit in the complex, the $C_8$ feed to the selective adsorption unit is processed to eliminate olefins and alkenyl aromatics such as styrene in the feed. Olefinic material can react and occlude the pores of the zeolite adsorbent. The olefinic material is removed by passing a $C_{8+}$ stream across a clay or acidic catalyst to react olefins and alkenyl aromatics with another (typically aromatic) molecule, forming heavier compounds ($C_{16+}$). These heavier compounds are typically removed from the mixed xylenes by fractionation. The heavy compounds cannot be processed in the TA/TDP unit due to their tendency to deactivate the catalyst and are generally removed from the complex as lower value fuels blend stock. As many of the heavy alkyl aromatic compounds fractionate with the fractions containing greater than 10 carbon atoms, they are not typically sent as feedstock to the transalkylation unit, and instead are sent to gasoline blending or used as fuel oil.

SUMMARY

A need has been recognized for the characterization and recovery of higher value light aromatics in the range from $C_6$ to $C_{10}$ from certain heavy compounds before processing aromatic streams through specialized product production units, such as the TA/TDP unit. Embodiments disclosed here include characterization of the products formed during the treatment of aromatics streams during processing of hydrocarbons. Certain embodiments include processes for recovery of alkyl mono-aromatic compounds. An embodiment of the process for recovery of alkyl mono-aromatic compounds includes the steps of (a) supplying a feed stream containing $C_{9+}$ compounds from an aromatic complex to a separator to produce a first product stream containing $C_9$ and $C_{10}$ compounds and a second product stream containing one or more of heavy alkyl aromatic compounds and alkyl-bridged non-condensed alkyl multi-aromatic compounds; (b) supplying the first product stream containing $C_9$ and $C_{10}$ compounds to a transalkylation/toluene disproportionation process unit to yield a third product stream enriched in $C_8$ compounds; (c) allowing a hydrogen stream and the second product stream to react in presence of a catalyst under specific reaction conditions in a hydrodearylation reactor to yield a fourth product stream containing one or more alkyl mono-aromatic compounds and a fifth product stream containing $C_{11+}$ compounds; and (d) supplying the fourth product stream to the toluene transalkylation/toluene disproportionation process unit to produce alkyl mono-aromatic compounds. In an embodiment, the fourth product stream and the first product stream containing $C_9$ and $C_{10}$ compounds are mixed to form a feed stream for the toluene transalkylation/toluene disproportionation process unit. The feed stream can be from a xylene rerun column of an aromatic recovery process. The feed stream can be undiluted by a solvent. A portion of the hydrogen stream may be supplied to a catalyst bed in the hydrodearylation reactor to quench the catalyst bed. The process can further include supplying the fourth product stream containing one or more alkyl mono-aromatic compounds to a separator to recover a benzene-containing stream; and supplying the benzene-containing stream to the toluene transalkylation/toluene disproportionation process unit to produce alkyl mono-aromatic compounds. The process can further include recovering a $C_8$ stream from the separator; and supplying the $C_8$ stream to a para-xylene unit to produce para-xylene. The process can further include recovering a $C_{9+}$ stream from the separator; and supplying the $C_{9+}$ stream to the toluene transalkylation/toluene disproportionation process unit to produce alkyl mono-aromatic compounds. The process can further include supplying the fourth product stream containing one or more alkyl mono-aromatic compounds to a separator to recover a toluene-containing stream; and supplying the toluene-containing stream to the toluene transalkylation/toluene disproportionation process unit to produce alkyl mono-aromatic compounds.

The catalyst in the hydrodearylation reactor can include a support made of one or more of silica, alumina, titania, and a combination thereof. The catalyst in the hydrodearylation reactor can further include an acidic component being at least one member of the group consisting of amorphous silica-alumina, zeolite, and combinations thereof. The zeolite can be one or more of or derived from FAU, *BEA, MOR, MFI, or MWW framework types, wherein each of these codes correspond to a zeolite structure present in the database of zeolite structures as maintained by the Structure Commission of the International Zeolite Association. The catalyst in the hydrodearylation reactor can include an IUPAC Group 6-10 metal that is at least one member of the group consisting of iron, cobalt, nickel, molybdenum, tungsten, and combinations thereof. The IUPAC Group 8-10 metal can be present ranging from 2 to 20 percent by weight of the catalyst and the IUPAC Group 6 metal can be present ranging from 1 to 25 percent by weight of the catalyst. The conditions in the hydrodearylation reactor can include an operating temperature in the range of about 200 to 450° C., or about 250 to 450° C. and an operating hydrogen partial pressure in the range of about 5 bar gauge to 100 bar gauge. One of the alkyl mono-aromatic compounds produced by the toluene transalkylation/toluene disproportionation is a para-xylene.

In some embodiments of the presently disclosed systems and methods, catalysts in addition to or alternative to catalyst supports, such as silica or zeolite catalysts and catalyst supports can contain 0 wt. % added metal catalyst, or a zeolite support system such as silica with an alumina binder contains 0 wt. % added metal catalyst. The catalyst in the hydrodearylation reactor can include an IUPAC Group 6-10 metal that is at least one member of the group consisting of iron, cobalt, nickel, molybdenum, tungsten, and combinations thereof. An IUPAC Group 8-10 metal can be present ranging from about 0 to 20 percent by weight of the catalyst and an IUPAC Group 6 metal can be present ranging from about 0 to 25 percent by weight of the catalyst. In some embodiments of the catalyst or a catalyst support no metal is present, but in others one or more metals are present. The conditions in the hydrodearylation reactor can include an operating temperature in the range of about 200 to 450° C., or about 250 to 450° C. and an operating hydrogen partial pressure in the range of about 5 bar gauge to 100 bar gauge. One of the alkyl mono-aromatic compounds produced by the toluene transalkylation/toluene disproportionation is a para-xylene.

In some embodiments, hydrocracking catalysts containing about 4 wt. % NiO and about 16 wt. % $MoO_3$ on Ti and Zr modified USY zeolite (10 wt. %) with a silica alumina binder (90 wt. %) can be used. However, in some embodiments only zeolite or only zeolite and a binder can be advantageously used to function as a hydrodearylation catalyst, without added catalytic metals such as IUPAC Group 6-10 metals.

Certain embodiments include systems for recovery of alkyl mono-aromatic compounds. An embodiment of a system for conversion of alkyl-bridged non-condensed alkyl multi-aromatic compounds to alkyl mono-aromatic compounds includes the following components: (i) a first separator adapted to receive a feed stream containing one or more of heavy alkyl aromatic compounds and one or more alkyl-bridged non-condensed alkyl multi-aromatic compounds having at least two benzene rings connected by an alkyl bridge group with at least two carbons and the benzene rings being connected to different carbons of the alkyl bridge group, and produces a first product stream containing $C_9$ and $C_{10}$ compounds and a second product stream containing one or more of heavy alkyl aromatic compounds and alkyl-bridged non-condensed alkyl multi-aromatic compounds; (ii) a hydrodearylation reactor fluidly coupled to the first separator and adapted to receive a hydrogen stream and the second product stream and to produce a third product stream in presence of a catalyst, the third product stream containing one or more alkyl mono-aromatic compounds; and (iii) a second separator fluidly coupled to the hydrodearylation reactor and adapted to receive the third product stream and to produce a benzene-containing stream, a toluene-containing stream, a $C_8$-rich stream, and a bottoms $C_{9+}$ stream. The system can also include a transalkylation unit fluidly coupled to the second separator and adapted to receive the first product stream and one or more of the benzene-containing stream, the toluene-containing stream, and the bottoms $C_{9+}$ stream, and to produce alkyl mono-aromatic compounds. The system can also include a para-xylene unit fluidly coupled to the second separator and adapted to receive the $C_8$-rich stream and to produce a para-xylene-rich stream.

BRIEF DESCRIPTION OF THE DRAWINGS

Embodiments will be readily understood by the following detailed description in conjunction with the accompanying drawings. Embodiments are illustrated by way of example and not by way of limitation in accompanying drawings.

DETAILED DESCRIPTION

Figure 1:
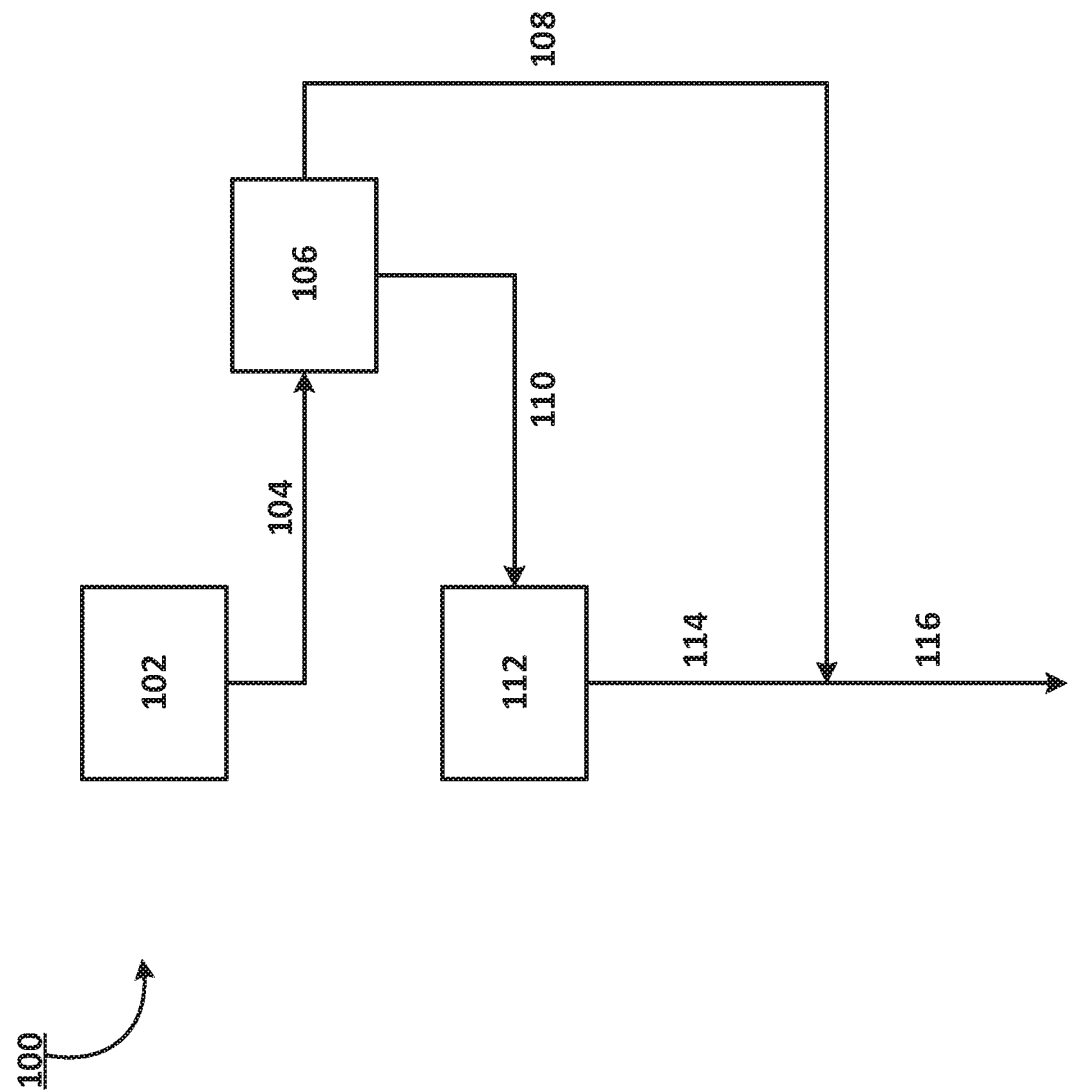
FIG. 1 is a schematic representation of certain components of an aromatics processing system that upgrades fuel oil to a petrochemical feedstock, according to an exemplary embodiment.

The present disclosure describes various embodiments related to processes, devices, and systems for conversion of alkyl-bridged non-condensed alkyl aromatic compounds to alkyl mono-aromatic compounds. Further embodiments are described and disclosed.

In the following description, numerous details are set forth in order to provide a thorough understanding of the various embodiments. In other instances, well-known processes, devices, and systems may not have been described in particular detail in order not to unnecessarily obscure the various embodiments. Additionally, illustrations of the various embodiments may omit certain features or details in order to not obscure the various embodiments. Here, reference is made to the accompanying drawings that form a part of this disclosure. The drawings may provide an illustration of some of the various embodiments in which the subject matter of the present disclosure may be practiced. Other embodiments may be utilized, and logical changes may be made without departing from the scope of this disclosure. Therefore, the following detailed description is not to be taken in a limiting sense.

The description may use the phrases "in some embodiments," "in various embodiments," "in an embodiment," or "in embodiments," which may each refer to one or more of the same or different embodiments. Furthermore, the terms "comprising," "including," "having," and the like, as used with respect to embodiments of the present disclosure, are synonymous.

As used in this disclosure, the term "hydrodearylation" refers to a process for cleaving of the alkyl bridge of non-condensed alkyl-bridged multi-aromatics or heavy alkyl aromatic compounds to form alkyl mono-aromatics, in the presence a catalyst and hydrogen.

As used in this disclosure, the term "stream" (and variations of this term, such as hydrocarbon stream, feed stream, product stream, and the like) may include one or more of various hydrocarbon compounds, such as straight chain, branched or cyclical alkanes, alkenes, alkadienes, alkynes, alkyl aromatics, alkenyl aromatics, condensed and non-condensed di-, tri- and tetra-aromatics, and gases such as hydrogen and methane, $C_{2+}$ hydrocarbons and further may include various impurities.

As used in this disclosure, the term "zone" refers to an area including one or more equipment, or one or more sub-zones. Equipment may include one or more reactors or reactor vessels, heaters, heat exchangers, pipes, pumps, compressors, and controllers. Additionally, an equipment, such as reactor, dryer, or vessels, further may include one or more zones.

As used in this disclosure, the term "rich" means an amount of at least 30% or greater, by mole percentage of a compound or class of compounds in a stream. Certain streams rich in a compound or class of compounds can contain about 50% or greater, by mole percentage of the particular compound or class of compounds in the streams. In certain cases, mole percentage may be replaced by weight percentage, in accordance with standard industry usage.

As used in this disclosure, the term "mixed xylenes" refers to a mixture containing one or more $C_8$ aromatics, including any one of the three isomers of di-methylbenzene and ethylbenzene. As used in this disclosure, the term "conversion" refers to the conversion of compounds containing multiple aromatic rings or mono-aromatic compounds with heavy ($C_{4+}$) alkyl groups boiling above 210° C. to mono-aromatic compounds with a lighter alkyl groups boiling below 210° C.

During hydrocarbon processing, compounds composed of an aromatic ring with one or more coupled alkyl groups containing three or more carbon molecules per alkyl group are formed. Formation of these compounds may be from processes used by petroleum refiners and petrochemical producers to produce aromatic compounds from non-aromatic hydrocarbons, such as catalytic reforming. As many of these heavy alkyl aromatic compounds fractionate with the fractions containing greater than 10 carbon atoms, they are not typically sent as feedstock to the transalkylation unit, and instead are sent to gasoline blending or used as fuel oil. The methods and systems disclosed here result in upgrading a low-value fuel oil to petrochemical feed.

Provided here is an embodiment of a process to fractionate an effluent stream of a xylene re-run column and supply it as a feed stream to a hydrodearylation unit. In an embodiment, this stream is either subsequently processed or used to upgrade the fuel oil components (heavy fraction) to petrochemical feedstock. Methods and system disclosed here create value by processing a reject/bottoms stream from an aromatic complex and by upgrading a significant proportion of fuel oil into petrochemical feedstock. In an embodiment, the $C_{9+}$ stream from a xylene re-run column is fractionated to remove $C_9$ and $C_{10}$, leaving a $C_{11+}$ stream, which is considered as a low-value fuel oil stream. The $C_9$ and $C_{10}$ stream is directed to a TA/TDP process unit to yield increased quantities of $C_8$ that can be further processed downstream to yield para-xylene. The $C_{11+}$ fuel oil stream is subjected to hydrodearylation and the hydrodearylated liquid products sent for processing in a transalkylation unit. The unconverted $C_{11+}$ (mainly condensed diaromatics) stream is directed as fuel oil.

Disclosed here is a process for recovery of alkyl mono-aromatic compounds that includes the following steps. A feed stream containing $C_{9+}$ compounds from an aromatic complex is supplied to a separator to produce a first product stream containing $C_9$ and $C_{10}$ compounds and a second product stream containing one or more of heavy alkyl aromatic compounds and alkyl-bridged non-condensed alkyl multi-aromatic compounds. In an embodiment, the feed stream is from a xylene rerun column of an aromatic recovery process. In certain embodiments, the feed stream is undiluted by solvents and is directly supplied to the separator. In an embodiment, the second product stream contains $C_{11+}$ compounds. This first product stream containing $C_9$ and $C_{10}$ compounds is supplied to a TA/TDP process unit to yield a third product stream enriched in $C_8$ compounds. The second product stream and a hydrogen stream are supplied to a hydrodearylation reactor to react in presence of a catalyst under specific reaction conditions to yield a fourth product stream containing $C_9$ and $C_{10}$ compounds and a fifth product stream containing unconverted $C_{11+}$ compounds. The fourth product stream is supplied further to a TA/TDP process unit to supply and produce alkyl mono-aromatic compounds. In certain embodiments, the $C_8$ content in the fourth product stream increases following the processing in the TA/TDP process unit. In certain embodiments, the fifth product stream containing unconverted $C_{11+}$ compounds can be recycled to the hydrodearylation reactor. In certain embodiments, the fourth product stream and the first product stream containing $C_9$ and $C_{10}$ compounds are mixed to form a feed stream for the TA/TDP process unit. In certain embodiments, the alkyl mono-aromatic compounds produced by the TA/TDP process unit is para-xylene. In certain embodiments, the hydrodearylated products are supplied to a separator to recover a benzene-containing stream. And this benzene-containing stream can be directed to an appropriate part of the TA/TPD process unit. In certain embodiments, the hydrodearylated products are supplied to a separator to recover a toluene-containing stream. And this toluene-containing stream can be directed to an appropriate part of the TA/TPD process unit.

In an embodiment, the feedstock to the hydrodearylation reactor (either whole or fractionated) is mixed with an excess of hydrogen gas in a mixing zone. A portion of the hydrogen gas is mixed with the feedstock to produce a hydrogen-enriched liquid hydrocarbon feedstock. This hydrogen-enriched liquid hydrocarbon feedstock and undissolved hydrogen is supplied to a flashing zone in which at least a portion of undissolved hydrogen is flashed, and the hydrogen is recovered and recycled. The hydrogen-enriched liquid hydrocarbon feedstock from the flashing zone is supplied as a feed stream to the hydrodearylation reactor. The hydrodearylated liquid product stream that is recovered from the hydrodearylation reactor is further processed as provided here.

In certain embodiments, the hydrogen stream is combined with the second product stream before being supplied to the hydrodearylation reactor. In certain embodiments, the hydrogen stream includes a recycled hydrogen stream and a makeup hydrogen stream. In certain embodiments, the hydrogen stream comprises at least 70% hydrogen by weight. The catalyst can be presented as a catalyst bed in the reactor. In certain embodiments, a portion of the hydrogen stream is fed to the catalyst bed in the reactor to quench the catalyst bed. In certain embodiments, the catalyst bed is comprised of two or more catalyst beds. The catalyst can include a support that is at least one member of the group consisting of silica, alumina, titania, and combinations thereof, and further includes an acidic component that is at least one member of the group consisting of amorphous silica-alumina, zeolite, and combinations thereof. The zeolite can be one or more of or derived from FAU, *BEA, MOR, MFI, or MWW framework types, wherein each of these codes correspond to a zeolite structure present in the database of zeolite structures as maintained by the Structure Commission of the International Zeolite Association. In certain embodiments, the catalyst includes an IUPAC Group 8-10 metal and an IUPAC Group 6 metal. In certain embodiments, the catalyst includes an IUPAC Group 8-10 metal that is at least one member of the group consisting of iron, cobalt, and nickel, and combinations thereof. The catalyst includes an IUPAC Group 6 metal that is at least one member of the group consisting of molybdenum and tungsten, and combinations thereof. In certain embodiments, the IUPAC Group 8-10 metal is 2 to 20 percent by weight of the catalyst and the IUPAC Group 6 metal is 1 to 25 percent by weight of the catalyst. In certain embodiments, the catalyst is comprised of nickel, molybdenum, ultrastable Y-type zeolite, and silica-alumina support.

In some embodiments of the presently disclosed systems and methods, catalysts in addition to or alternative to catalyst supports, such as silica or zeolite catalysts and catalyst supports can contain 0 wt. % added metal catalyst, or a zeolite support system such as silica with an alumina binder contains 0 wt. % added metal catalyst. The catalyst in the hydrodearylation reactor can include an IUPAC Group 6-10 metal that is at least one member of the group consisting of iron, cobalt, nickel, molybdenum, tungsten, and combinations thereof. An IUPAC Group 8-10 metal can be present ranging from about 0 to 20 percent by weight of the catalyst and an IUPAC Group 6 metal can be present ranging from about 0 to 25 percent by weight of the catalyst. In some embodiments of the catalyst or a catalyst support no metal is present, but in others one or more metals are present. The conditions in the hydrodearylation reactor can include an operating temperature in the range of about 200 to 450° C., or about 250 to 450° C. and an operating hydrogen partial pressure in the range of about 5 bar gauge to 100 bar gauge. One of the alkyl mono-aromatic compounds produced by the toluene transalkylation/toluene disproportionation is a para-xylene.

In some embodiments, hydrocracking catalysts containing about 4 wt. % NiO and about 16 wt. % $MoO_3$. on Ti and Zr modified USY zeolite (10 wt. %) with a silica alumina binder (90 wt. %) can be used. However, in some embodiments only zeolite or only zeolite and a binder can be advantageously used to function as a hydrodearylation catalyst, without added catalytic metals such as IUPAC Group 6-10 metals.

In certain embodiments, the specific reaction conditions include an operating temperature of the reactor during the hydrodearylation reaction that is in the range of 200 to 450° C. In certain embodiments, the specific reaction conditions include an operating temperature of the reactor during the hydrodearylation reaction that is in the range of 250 to 350° C. In certain embodiments, the specific reaction conditions include an operating temperature of the reactor during the hydrodearylation reaction that is in the range of 300 to 350° C. The specific reaction conditions can include a hydrogen partial pressure of the reactor during the hydrodearylation reaction that is in the range of 5 to 100 bar gauge. In certain embodiments, the specific reaction conditions can include a hydrogen partial pressure of the reactor during the hydrodearylation reaction that is in the range of 50 to 100 bar gauge. In certain embodiments, the specific reaction conditions can include a hydrogen partial pressure of the reactor during the hydrodearylation reaction that is in the range of 5 to 80 bar gauge. In certain embodiments, the specific reaction conditions can include a hydrogen partial pressure of the reactor during the hydrodearylation reaction that is in the range of 5 to 30 bar gauge. The hydrogen partial pressure of the reactor during the hydrodearylation reaction can be maintained at less than 20 bar gauge. The specific reaction conditions can include a feed rate of the hydrogen stream that is in the range of 100 to 1000 standard liter per liter of feedstock. The specific reaction conditions can include a feed rate of the hydrogen stream that is in the range of 100 to 300 standard liter per liter of feedstock.

In an embodiment, a system is provided for conversion of alkyl-bridged non-condensed alkyl multi-aromatic compounds to alkyl mono-aromatic compounds. The system includes (i) a first separator that receives a feed stream containing one or more of heavy alkyl aromatic compounds and one or more alkyl-bridged non-condensed alkyl multi-aromatic compounds having at least two benzene rings connected by an alkyl bridge group with at least two carbons and the benzene rings that is connected to different carbons of the alkyl bridge group, and produces a first product stream containing $C_9$ and $C_{10}$ compounds and a second product stream containing one or more of heavy alkyl aromatic compounds and alkyl-bridged non-condensed alkyl multi-aromatic compounds; (ii) a hydrodearylation reactor fluidly coupled to the first separator and adapted to receive a hydrogen stream and the second product stream and to produce a third product stream in presence of a catalyst, and the third product stream containing one or more alkyl mono-aromatic compounds; (iii) a second separator fluidly coupled to the hydrodearylation reactor and adapted to receive the third product stream and to produce a benzene-containing stream, a toluene-containing stream, a $C_8$-rich stream, and a bottoms $C_{9+}$ stream. In certain embodiments, the system further includes a transalkylation unit that is adapted to receive the toluene-containing stream and the bottoms $C_{9+}$ stream and to produce alkyl mono-aromatic compounds. In order to increase the production of benzene and para-xylene, the toluene and $C_9$ and $C_{10}$ aromatics are processed within the complex through a toluene, $C_9$, $C_{10}$ transalkylation/toluene disproportionation (TA/TDP) process unit to produce benzene and xylenes. Any remaining toluene, $C_9$, and $C_{10}$ aromatics are recycled to extinction. In certain embodiments, the second product stream is a $C_{11+}$ stream. In certain embodiments, the alkyl mono-aromatic compounds produced by the transalkylation unit includes para-xylene.

A typical refinery with an aromatic complex contains the following units: an atmospheric distillation unit, a diesel hydrotreating unit, an atmospheric residue unit, a naphtha hydrotreating unit, a naphtha reforming unit and an aromatics complex. The whole crude oil is distilled in an atmospheric distillation column to recover a naphtha fraction (compounds with a boiling point ranging from 36° C. to 180° C.), diesel fraction (compounds with a boiling point ranging from 180° C. to 370° C.) and atmospheric residue fraction (compounds with a boiling point at 370° C. or higher). The naphtha fraction is hydrotreated in a naphtha hydrotreating unit to reduce the sulfur and nitrogen content to less than 0.5 part per million by weight and the hydrotreated naphtha fraction is sent to a catalytic reforming unit to improve its quality, such as, an increase in the octane number to produce gasoline blending stream or feedstock for an aromatics recovery unit. Similarly, the diesel fraction is hydrotreated in a separate hydrotreating unit to desulfurize the diesel oil to obtain diesel fraction meeting the stringent specifications of sulfur content that is less than 10 parts per million. The atmospheric residue fraction is either used a fuel oil component or sent to other separation/conversion units to convert low value hydrocarbons to high value products. The reformate fraction from the catalytic reforming unit can be used as gasoline blending component or sent to an aromatic complex to recover high value aromatics, such as, benzene, toluene, and xylenes. The reformate fraction from catalytic reforming unit is split into two fractions: light and heavy reformate. The light reformate is sent to a benzene extraction unit to extract the benzene and recover gasoline that is substantially free of benzene. The heavy reformate stream is sent to a para-xylene (p-xylene) extraction unit to recover p-xylene. Other xylenes that are recovered from the p-xylene unit are sent to a xylene isomerization unit to convert them to p-xylene. The converted fraction is recycled to the p-xylene extraction unit. The heavy fraction from the p-xylene extraction unit is recovered as a process reject or bottoms stream. The aromatics bottoms fraction from an aromatic recovery complex is processed in two ways. One, the aromatics bottoms fraction is fractionated into a 180-° C. fraction ((compounds with a boiling point less than 180° C.) and sent to a gasoline pool as blending components, and a 180+° C. fraction sent to a hydrodearylation unit. Alternatively, the aromatics bottoms fraction is sent directly to a hydrodearylation unit to recover light alkyl mono-aromatic compounds from heavy alkyl aromatic and alkyl-bridged non-condensed alkyl aromatic compounds. A typical system for aromatic transalkylation to ethylbenzene and xylenes includes the following components: a first transalkylation reactor, a series of separators, a second transalkylation reactor, a stabilizer, and a p-xylene production unit. The feed stream to the first transalkylation reactor is a mixture of a $C_{9+}$ alkyl aromatics mixture and benzene. This feed stream in brought into contact with a zeolite catalyst in the first transalkylation reactor. The effluent stream from this transalkylation reactor is directed to a separation column. This effluent stream may be combined with effluent streams from the second transalkylation reactor before entry into a separation column. There are three exit streams from the separation column: an overhead stream containing benzene, a bottoms stream of $C_{8+}$ aromatics including ethylbenzene and xylenes, and a side-cut stream containing toluene. The overhead stream is recycled to the first transalkylation reactor. The bottoms stream is supplied to a second separation column. An overhead stream containing ethylbenzene and xylenes from the second separation column is directed to a para-xylene unit to produce a para-xylene product stream and a bottoms stream of $C_{9+}$ alkylaromatics. The side-cut stream from the separation column is recycled to a second transalkylation unit with or without the recovery of toluene. This side-cut stream from the separation column can be combined with bottoms stream from second separation column to form a combined stream that is supplied to a third separation column. This separation column separates the combined stream into a bottoms stream of $C_{11+}$ alkylaromatics ("heavies") and an overhead stream of $C_9$, $C_{10}$ alkylaromatics, and lighter compounds (including $C_7$ alkylaromatics) directed to a second transalkylation unit. Hydrogen is also supplied to the second transalkylation unit. Here, in the second transalkylation unit, the overhead stream and hydrogen are brought in contact with a transalkylation catalyst, and the effluent stream is directed to a stabilizer column. Two streams exit the stabilizer column: an overhead stream of light end hydrocarbons (generally comprising at least ethane) and a bottom stream of a second transalkylation product.

As previously described, the aromatic bottoms stream from an aromatic recovery complex can be directly supplied to a hydrodearylation unit and a hydrodearylated liquid product stream can be recovered for further processing. In an embodiment 100 as described in FIG. 1, the aromatic bottoms stream 104 from an aromatic recovery complex 102 is sent to a separator 106. In an embodiment, this separator 106 can be a separation unit including a distillation column with 5 or more theoretical trays. In an embodiment, the separator 106 can be a flash vessel or a stripper. Two streams exit the separator 106: an overhead stream 108 containing $C_9$ and $C_{10}$ compounds and a bottoms stream 110 containing $C_{11+}$ compounds. In an embodiment, the overhead stream 108 contains about 50-99 wt. % of the $C_9$ and $C_{10}$ compounds. In another embodiment, the overhead stream 108 contains about 60-99 wt. % of the $C_9$ and $C_{10}$ compounds. In an embodiment, the overhead stream 108 contains about 80-99 wt. % of the $C_9$ and $C_{10}$ compounds. For example, simulated distillation data indicated that the overhead stream 108 contains about 90-99 wt. % of the $C_9$ and $C_{10}$ compounds. And this data aligned with the two-dimensional gas chromatography data obtained in this instance, which revealed the stream 104 as containing about 91 wt. % of the $C_9$ and $C_{10}$ compounds. The $C_{9+}$ feed from a refinery can be "heavy" with a different composition. In other instances, the $C_9$ and $C_{10}$ compounds made up about 68 wt. % of the feed as determined by two-dimensional gas chromatography. The bottoms stream 110 containing $C_{11+}$ compounds is directed to a hydrodearylation unit 112 for processing into a hydrodearylated liquid product stream 114. In an embodiment, the bottoms stream 110 contains about 5-99 wt. % of $C_{11+}$ compounds. In another embodiment, the bottoms stream 110 contains about 30-99 wt. % of $C_{11+}$ compounds. In an embodiment, the bottoms stream 110 contains about 80-99 wt. % of $C_{11+}$ compounds. In an embodiment, the hydrodearylated liquid product stream 114 contains greater than 10 wt. % of alkyl mono-aromatic compounds. In an embodiment, the hydrodearylated liquid product stream 114 contains greater than 20 wt. % of alkyl mono-aromatic compounds. In an embodiment, the hydrodearylated liquid product stream 114 contains greater than 40 wt. % of alkyl mono-aromatic compounds. In an embodiment, the hydrodearylated liquid product stream 114 contains about 50 wt. % of alkyl mono-aromatic compounds. In an embodiment, the hydrodearylated liquid product stream 114 contains about 70 wt. % of alkyl mono-aromatic compounds. In an embodiment, the hydrodearylated liquid product stream 114 contains about 90 wt. % of alkyl mono-aromatic compounds. In an embodiment, the hydrodearylated liquid product stream 114 contains less than 70 wt. % of di-aromatic compounds. In an embodiment, the hydrodearylated liquid product stream 114 contains less than 50 wt. % of di-aromatic compounds. In an embodiment, the hydrodearylated liquid product stream 114 contains less than 40 wt. % of di-aromatic compounds. In an embodiment, the hydrodearylated liquid product stream 114 contains less than 20 wt. % of di-aromatic compounds. In an embodiment, the hydrodearylated liquid product stream 114 contains less than 10 wt. % of di-aromatic compounds. In an embodiment, the hydrodearylated liquid product stream 114 contains less than 1 wt. % of di-aromatic compounds. The overhead stream 108 containing $C_9$ and $C_{10}$ compounds is combined with the hydrodearylated liquid product stream 114 leaving the hydrodearylation unit, and this combined stream 116 is supplied to a transalkylation reactor for further processing.

Figure 2:
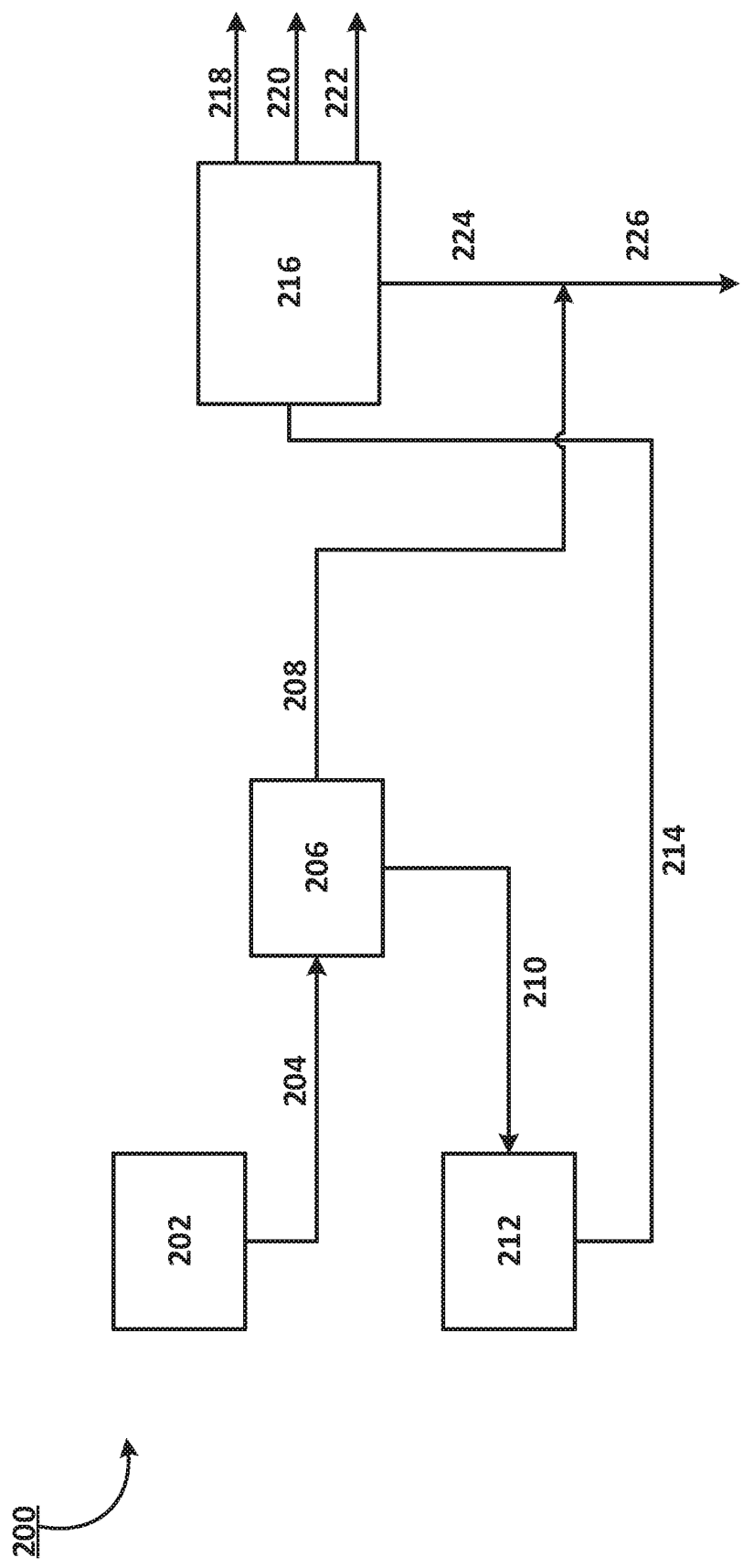
FIG. 2 is a schematic representation of certain components of an aromatics processing system that upgrades fuel oil to a petrochemical feedstock, according to an exemplary embodiment.

In another embodiment, the aromatic bottoms stream from an aromatic recovery complex is sent to a separator. In an embodiment, this separator can be a separation unit including a distillation column with 5 or more theoretical trays. In an embodiment, the separator can be a flash vessel or a stripper. In an embodiment 200 as described in FIG. 2, the aromatic bottoms stream 204 from an aromatic recovery complex 202 is sent to a first separator 206. Two streams exit the first separator 206: an overhead stream 208 containing $C_9$ and $C_{10}$ compounds and a bottoms stream 210 containing $C_{11+}$ compounds. In an embodiment, the overhead stream 208 contains about 50-99 wt. % of the $C_9$ and $C_{10}$ compounds. In another embodiment, the overhead stream 208 contains about 60-99 wt. % of the $C_9$ and $C_{10}$ compounds. In an embodiment, the overhead stream 208 contains about 80-99 wt. % of the $C_9$ and $C_{10}$ compounds. In an embodiment, the overhead stream 208 contains about 90-99 wt. % of the $C_9$ and $C_{10}$ compounds. The bottoms stream 210 containing $C_{11+}$ compounds is directed to a hydrodearylation unit 212 for processing a hydrodearylated liquid product stream 214. In an embodiment, the bottoms stream 210 contains about 5-99 wt. % of $C_{11+}$ compounds. In another embodiment, the bottoms stream 210 contains about 30-99 wt. % of $C_{11+}$ compounds. In an embodiment, the bottoms stream 210 contains about 80-99 wt. % of $C_{11+}$ compounds. The hydrodearylated liquid product stream 214 is supplied to a second separator 216. In an embodiment, the hydrodearylated liquid product stream 214 contains about 10 wt. % of alkyl mono-aromatic compounds. In an embodiment, the hydrodearylated liquid product stream 214 contains about 20 wt. % of alkyl mono-aromatic compounds. In an embodiment, the hydrodearylated liquid product stream 214 contains about 40 wt. % of alkyl mono-aromatic compounds. In an embodiment, the hydrodearylated liquid product stream 214 contains about 50 wt. % of alkyl mono-aromatic compounds. In an embodiment, the hydrodearylated liquid product stream 214 contains about 70 wt. % of alkyl mono-aromatic compounds. In an embodiment, the hydrodearylated liquid product stream 214 contains about 90 wt. % of alkyl mono-aromatic compounds. In an embodiment, the hydrodearylated liquid product stream 214 contains less than 70 wt. % of di-aromatic compounds. In an embodiment, the hydrodearylated liquid product stream 214 contains less than 40 wt. % of di-aromatic compounds. In an embodiment, the hydrodearylated liquid product stream 214 contains less than 20 wt. % of di-aromatic compounds. In an embodiment, the hydrodearylated liquid product stream 214 contains less than 10 wt. % of di-aromatic compounds. In an embodiment, the hydrodearylated liquid product stream 214 contains less than 1 wt. % of di-aromatic compounds. The hydrodearylated liquid product stream 214 is supplied to a second separator 216. Four streams exit the second separator 216: a benzene-containing stream 218, a toluene-containing stream 220, a $C_8$-containing stream 222, and a bottoms $C_{9+}$ stream 224. In an embodiment, the benzene-containing stream 218 contains less than 30 wt. % of benzene. In another embodiment, the benzene-containing stream 218 contains less than 20 wt. % of benzene. In another embodiment, the benzene-containing stream 218 contains less than 10 wt. % of benzene. In another embodiment, the benzene-containing stream 218 contains less than 5 wt. % of benzene. The toluene-containing stream 220 can be directed to a transalkylation reactor as a feed stream. In the transalkylation reactor, the toluene is combined with a $C_{9+}$ stream to produce alkyl mono-aromatic compounds. In an embodiment, the toluene-containing stream 220 contains less than 30 wt. % of toluene. In another embodiment, the toluene-containing stream 220 contains less than 20 wt. % of toluene. In another embodiment, the toluene-containing stream 220 contains less than 15 wt. % of toluene. In another embodiment, the toluene-containing stream 220 contains less than 10 wt. % of toluene. The $C_8$-containing stream 222 is directed to the p-xylene production unit. In an embodiment, the $C_8$-containing stream 222 contains less than 30 wt. % of $C_8$ compounds, such as xylene and ethylbenzene. In another embodiment, the $C_8$-containing stream 222 contains less than 20 wt. % of these $C_8$ compounds. In another embodiment, the $C_8$-containing stream 222 contains less than 10 wt. % of these $C_8$ compounds. The $C_{9+}$ stream 224 can be supplied as part of a feed stream 226 to a transalkylation unit. In an embodiment, the $C_{9+}$ stream 224 is combined with the overhead stream 208 containing $C_9$ and $C_{10}$ compounds and supplied as part of a feed stream 226 to the transalkylation unit.

Figure 3:
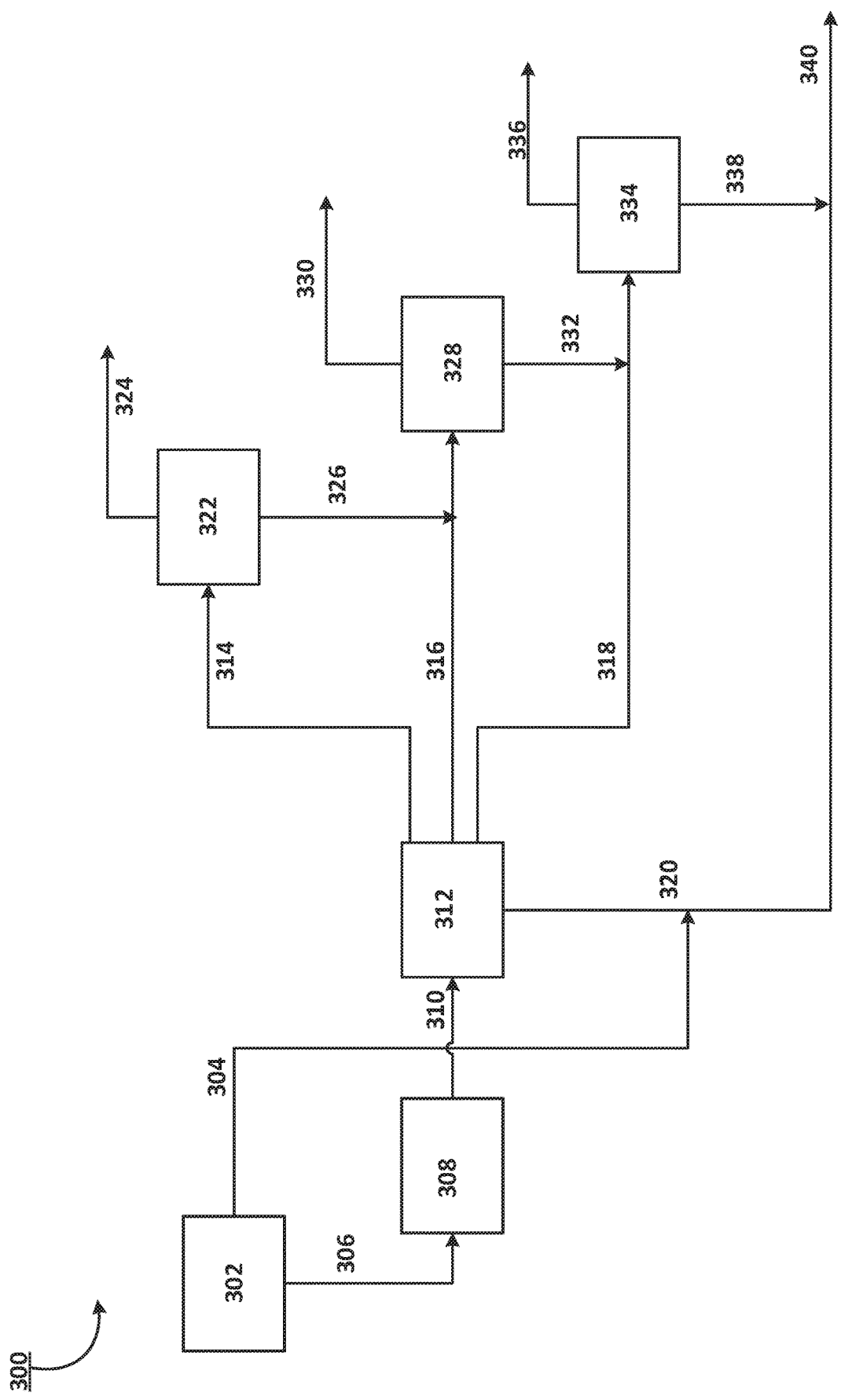
FIG. 3 is a schematic representation of certain components of an aromatics processing system that upgrades fuel oil to a petrochemical feedstock, according to an exemplary embodiment.

In an embodiment 300 as described in FIG. 3, the aromatic bottoms stream from an aromatic recovery complex is sent to a first separator 302. Two streams exit the first separator 302: an overhead stream 304 containing $C_9$ and $C_{10}$ compounds and a bottoms stream 306 containing $C_{11+}$ compounds. In an embodiment, the overhead stream 304 contains about 50-99 wt. % of the $C_9$ and $C_{10}$ compounds. In another embodiment, the overhead stream 304 contains about 60-99 wt. % of the $C_9$ and $C_{10}$ compounds. In an embodiment, the overhead stream 304 contains about 80-99 wt. % of the $C_9$ and $C_{10}$ compounds. For example, simulated distillation data indicated that the overhead stream 304 contains about 90-99 wt. % of the $C_9$ and $C_{10}$ compounds.

In an embodiment, the overhead stream 304 containing $C_9$ and $C_{10}$ compounds can be supplied as part of a feed stream 320 to a transalkylation unit. The bottoms stream 306 containing $C_{11+}$ compounds is directed to a hydrodearylation unit 308 for processing into a hydrodearylated liquid product stream 310. In an embodiment, the bottoms stream 306 contains about 5-99 wt. % of $C_{11+}$ compounds. In another embodiment, the bottoms stream 306 contains about 30-99 wt. % of $C_{11+}$ compounds. In an embodiment, the bottoms stream 306 contains about 80-99 wt. % of $C_{11+}$ compounds. The hydrodearylated liquid product stream 310 is sent to a second separator 312. In an embodiment, the hydrodearylated liquid product stream 310 contains about 10 wt. % of alkyl mono-aromatic compounds. In an embodiment, the hydrodearylated liquid product stream 310 contains about 20 wt. % of alkyl mono-aromatic compounds. In an embodiment, the hydrodearylated liquid product stream 310 contains about 40 wt. % of alkyl mono-aromatic compounds. In an embodiment, the hydrodearylated liquid product stream 310 contains about 50 wt. % of alkyl mono-aromatic compounds. In an embodiment, the hydrodearylated liquid product stream 310 contains about 70 wt. % of alkyl mono-aromatic compounds. In an embodiment, the hydrodearylated liquid product stream 310 contains about 90 wt. % of alkyl mono-aromatic compounds. In an embodiment, the hydrodearylated liquid product stream 310 contains less than 70 wt. % of di-aromatic compounds. In an embodiment, the hydrodearylated liquid product stream 310 contains less than 40 wt. % of di-aromatic compounds. In an embodiment, the hydrodearylated liquid product stream 310 contains less than 20 wt. % of di-aromatic compounds. In an embodiment, the hydrodearylated liquid product stream 310 contains less than 10 wt. % of di-aromatic compounds. In an embodiment, the hydrodearylated liquid product stream 310 contains less than 1 wt. % of di-aromatic compounds.

Four streams exit the second separator 312: a benzene-containing stream 314, a first toluene-containing stream 316, a first $C_8$-containing stream 318, and a bottoms $C_{9+}$ stream 320. In an embodiment, the benzene-containing stream 314 contains less than 30 wt. % of benzene. In another embodiment, the benzene-containing stream 314 contains less than 20 wt. % of benzene. In another embodiment, the benzene-containing stream 314 contains less than 10 wt. % of benzene. In another embodiment, the benzene-containing stream 314 contains less than 5 wt. % of benzene. In an embodiment, the first toluene-containing stream 316 contains less than 30 wt. % of toluene. In another embodiment, the first toluene-containing stream 316 contains less than 20 wt. % of toluene. In another embodiment, the first toluene-containing stream 316 contains less than 15 wt. % of toluene. In another embodiment, the first toluene-containing stream 316 contains less than 10 wt. % of toluene.

In an embodiment, the first $C_8$-containing stream 318 contains less than 30 wt. % of $C_8$ compounds, such as xylene and ethylbenzene. In another embodiment, the first $C_8$-containing stream 318 contains less than 20 wt. % of these $C_8$ compounds. In another embodiment, the first $C_8$-containing stream 318 contains less than 10 wt. % of these $C_8$ compounds.

In an embodiment, the bottoms $C_{9+}$ stream is supplied as part of a feed stream 320 to a transalkylation unit. The benzene-containing stream 314 is sent to a third separator 322. Two streams exit the third separator 322: a benzene-enriched stream 324 that is directed to a transalkylation reactor, and a second toluene-containing stream 326 that is directed to a fourth separator 328, either as a separate feed stream or as a mixture with the first toluene-containing stream 316. The first toluene-containing stream 316 can be supplied independently to the fourth separator 328. Two streams exit the fourth separator 328: a toluene-enriched stream 330 that is directed to a transalkylation reactor, and a second $C_8$-containing stream 332 that is directed to a fifth separator 334, either as a separate feed stream or as a mixture with the first $C_8$-rich stream 318. The first $C_8$-rich stream 318 can be supplied independently to the fifth separator 334. Two streams exit the fifth separator 334: a $C_8$-rich stream 336 that is directed to a p-xylene production unit, and a $C_{9+}$-containing stream 338 that is directed to the transalkylation unit, either as a separate feed stream or as a mixture with the bottoms $C_{9+}$ stream 320. In an embodiment, the $C_{9+}$-containing stream 338 is combined with the overhead stream 304 containing $C_9$ and $C_{10}$ compounds from the first separator 302 and supplied as a feed stream 340 to the transalkylation unit. In another embodiment, the overhead stream 304 containing $C_9$ and $C_{10}$ compounds from the first separator 302, the bottoms $C_{9+}$ stream 320 from the second separator 312, and the $C_{9+}$-containing stream 338 from the fifth separator 334 are combined and supplied as a feed stream 340 to a transalkylation unit. In another embodiment, each of these streams can be separately supplied to the first transalkylation unit.

Figure 4:
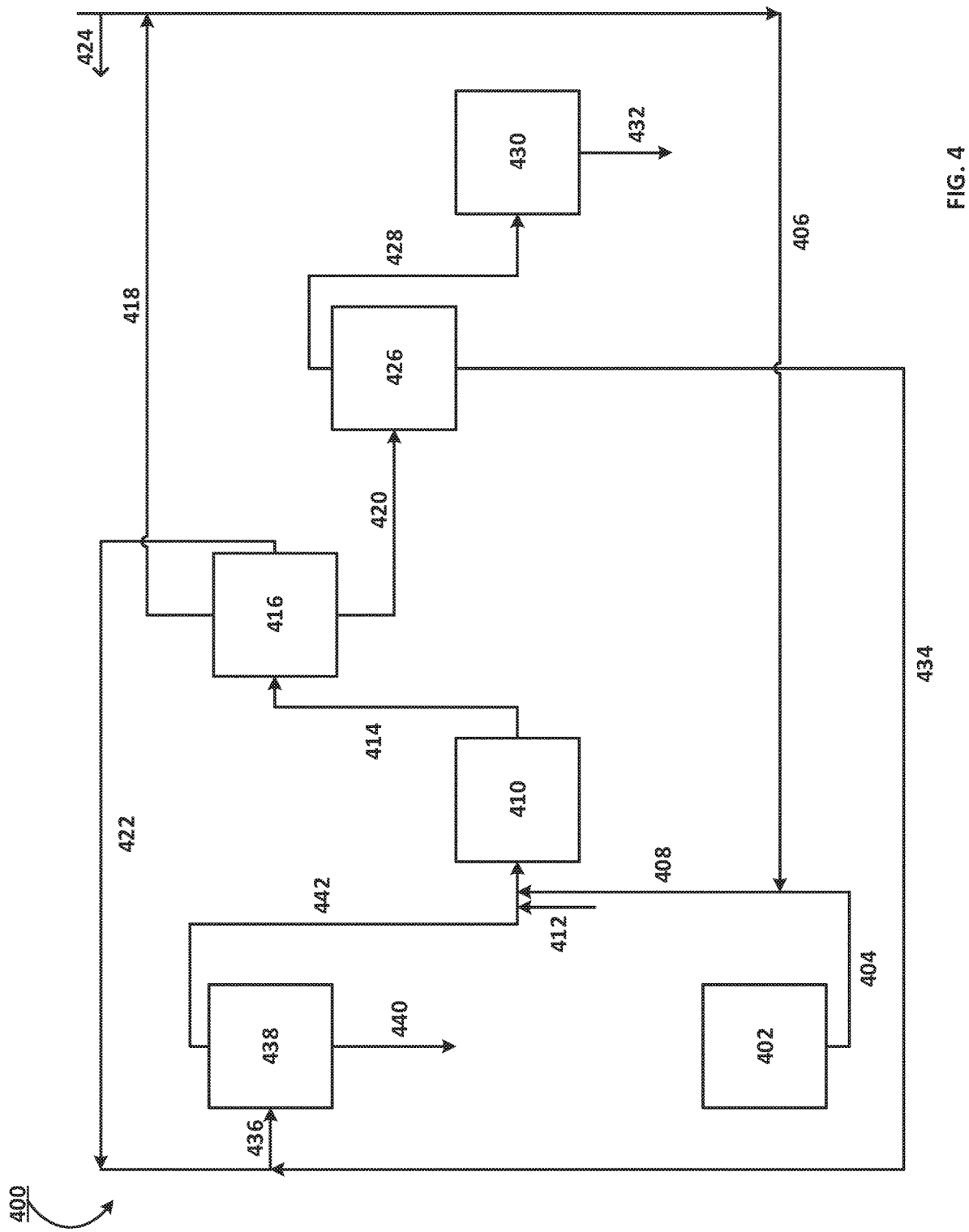
FIG. 4 is a schematic representation of certain components of an aromatics processing system that upgrades fuel oil to a petrochemical feedstock, according to an exemplary embodiment.

Described here is a method and a system used for aromatic transalkylation to ethylbenzene and xylenes. In an embodiment 400 as described in FIG. 4, the aromatic bottoms stream from an aromatic recovery complex is sent to a hydrodearylation unit 402. The hydrodearylated liquid product stream 404, exiting from the hydrodearylation unit 402, may also contain benzene, toluene and $C_8$ compounds, along with $C_{9+}$ alkyl aromatics. The hydrodearylated liquid product stream 404 is mixed with a benzene-containing stream 406 to form a feed stream 408. The feed stream 408 is supplied to a transalkylation reactor 410 either with or without an additional hydrogen stream 412. The feed stream 408 in the presence of a catalyst is converted to a first product stream 414 containing benzene, $C_{8+}$ aromatics including ethylbenzene and xylenes, and toluene. The first product stream 414 from the transalkylation reactor is directed to a first separation column 416. The first product stream 414 is separated into three fractions: a first overhead stream 418 containing benzene, a first bottoms stream 420 containing $C_{8+}$ aromatics including ethylbenzene and xylenes, and a side-cut stream 422 containing toluene. The overhead stream 418 is recycled to the first transalkylation unit after benzene is removed via stream 424. The first bottoms stream 420 of $C_{8+}$ aromatics, including ethylbenzene and xylenes, from the first separation column 416 is directed to a second separation column 426. Two streams are recovered from this second separation column 426: a second overhead stream 428 of ethylbenzene and xylenes, which is directed to a para-xylene unit 430 to produce a para-xylene-rich stream 432, and a second bottoms stream 434 of $C_{9+}$ alkylaromatics. The side-cut stream 422 from the first separation column 416 is supplied as part of a feed stream 436 to a third separation column 438 after additional toluene is added or removed (not shown in FIG. 4). Toluene is normally recycled to extinction by reacting with $C_9$ and $C_{10}$ to produce benzene and $C_8$. If there is a decrease or lack of toluene in the system, make-up toluene may be required. If there is a decrease or lack of $C_9/C_{10}$, the amount of toluene can be proportionately reduced to make the stoichiometry. Certain market conditions may influence the removal of toluene from the system. The side-cut stream 422 is mixed with the second bottoms stream 434 of $C_{9+}$ alkylaromatics to form a combined feed stream 436 that is supplied to the third separation column 438. Two streams are recovered from this third separation column 438: a third bottoms stream 440 of $C_{11+}$ alkylaromatics and an overhead stream 442 of $C_9$ and $C_{10}$ alkylaromatics and lighter compounds (including $C_7$ alkylaromatics) directed to the transalkylation unit 410. In certain embodiments, the unconverted products can be recycled to the hydrodearylation unit 402 (not shown in FIG. 4).

Described here are processes and systems to fractionate the reject/bottoms stream of a xylene re-run column and to upgrade the fuel oil components (heavy fraction) to petrochemical feedstock. Also described are embodiments to upgrade the as-received reject/bottoms stream from the xylene re-run column. The $C_{9+}$ stream from a xylene re-run column is fractionated to remove $C_9$ and $C_{10}$, leaving a $C_{11+}$ stream, which is considered as a low-value fuel oil stream. The $C_9$ and $C_{10}$ stream is directed to a TA/TDP process unit to be processed to yield increased quantities of $C_8$ that can be further processed downstream to yield para-xylene. The $C_{11+}$ fuel oil stream is subjected to hydrodearylation. The unconverted $C_{11+}$ (mainly condensed diaromatics) stream is directed as fuel oil (approximately 25 wt. % of the original fuel oil stream). The methods and systems disclosed here allow a low-value fuel oil stream to be upgraded into petrochemical feedstock. Approximately 75% of the fuel oil is converted to isomer grade mixed xylenes.

EXAMPLES

A couple of methods and systems for integration of a hydrodearylation process with a transalkylation process are illustrated here. While the particular example provided below is for a stream containing $C_{9+}$ compounds, the methods and systems for integration of a hydrodearylation process with a transalkylation process can utilize a $C_{11+}$ feed.

Example 1

About 7.97 kilograms of an aromatic bottoms fraction, derived from a non-fractionated $C_{9+}$ feed, was distilled using a lab-scale true boiling point distillation column with 15 or more theoretical plate using the ASTM D2892 method. The feed stream contains about 83 weight percent (wt. %) of a gasoline fraction (compounds with a boiling point ranging from 36° C. to 180° C.) and about 17 wt. % of a residue fraction (compounds with a boiling point above 180° C.).

Properties and composition of the feed stream are shown in Tables 1 and 2.

TABLE 1

| Property | Feedstock Aromatics Bottoms | Gasoline Fraction | Residue Fraction |
|---|---|---|---|
| Density | 0.8834 | 0.8762 | 0.9181 |
| Octane Number ASTM D2799 | Not applicable | 108 | Not applicable |

TABLE 2

| Property | Boiling Point, ° C. (Feedstock Aromatics Bottoms) | Boiling Point, ° C. (Gasoline Fraction) | Boiling Point, ° C. (Residue Fraction) |
|---|---|---|---|
| Initial Boiling Point | 153 | 154 | 163 |
| 10 wt. % | 163 | 164 | 190 |
| 30 wt. % | 166 | 166 | 202 |
| 50 wt. % | 172 | 171 | 231 |
| 70 wt. % | 175 | 174 | 289 |
| 90 wt. % | 191 | 183 | 324 |
| Final Boiling point | 337 | 204 | 359 |

In an example of a hydrodearylation process, a feedstock consisting of a non-fractionated xylene rerun column bottoms stream with the above described properties was treated in a hydrodearylation reaction zone containing a catalyst having nickel and molybdenum with ultrastable Y-type (USY) zeolite on a silica-alumina support operated at hydrodearylation conditions including a temperature ranging from 280 to 340° C., at a hydrogen partial pressure of 15 or 30 bar, a liquid hourly space velocity of 1.7 $hr^{-1}$. Feed and hydrodearylated liquid product compositions, as analyzed by two-dimensional gas chromatography, are provided in Table 3.

Key for Table 2—MA: Mono Aromatics; NMA: Naphtheno Mono Aromatics; MN: Mono-Naphthenes; DN: Di-naphthenes; P: Paraffins; NDA: Naphtheno Di Aromatics; DA: Diaromatics; and TrA: Tri Aromatics For example, subjecting the feed to hydrodearylation conditions in the presence of the catalyst and hydrogen at 320° C. and 30 bar, there is an approximately 75% reduction in diaromatic content. The decrease in the diaromatic content demonstrates that hydrodearylation has occurred and the low-value heavy components of the stream have been upgraded to higher value components. The technology also takes a low-value fuel oil from an aromatic bottoms/reject stream from an aromatic complex and upgrades the fuel oil to petrochemical feedstock.

Ranges may be expressed herein as from about one particular value and to about another particular value. When such a range is expressed, it is to be understood that another embodiment is from the one particular value and/or to the other particular value, along with all combinations within said range. Where the range of values is described or referenced here, the interval encompasses each intervening value between the upper limit and the lower limit as well as the upper limit and the lower limit and includes smaller ranges of the interval subject to any specific exclusion provided. Where a method comprising two or more defined steps is recited or referenced herein, the defined steps can be carried out in any order or simultaneously except where the context excludes that possibility. While various embodiments have been described in detail for the purpose of illustration, they are not to be construed as limiting, but are intended to cover all the changes and modifications within the spirit and scope thereof

What is claimed is:

1. A system for conversion of alkyl-bridged non-condensed alkyl multi-aromatic compounds to alkyl mono-aromatic compounds, the system comprising:
   a first separator adapted to receive a feed stream containing one or more of heavy alkyl aromatic compounds and one or more alkyl-bridged non-condensed alkyl multi-aromatic compounds having at least two benzene rings connected by an alkyl bridge group with at least two carbons and the benzene rings being connected to different carbons of the alkyl bridge group, and produces a first product stream containing $C_9$ and $C_{10}$ compounds and a second product stream containing one or more of heavy alkyl aromatic compounds and alkyl-bridged non-condensed alkyl multi-aromatic compounds;
   a hydrodearylation reactor fluidly coupled to the first separator and adapted to receive a hydrogen stream and the second product stream and to produce a third

TABLE 3

| Run # | Temperature ° C. | Pressure Bar | MA Wt. % | NMA Wt. % | MN Wt. % | DN Wt. % | P Wt. % | NDA Wt. % | DA Wt. % | TrA Wt. % |
|---|---|---|---|---|---|---|---|---|---|---|
| Feed | 0 | 0 | 92.28 | 1.82 | 0.15 | 0.12 | 0.37 | 0.59 | 4.34 | 0.33 |
| 1 | 340 | 30 | 91.67 | 2.91 | 2.1 | 0.43 | 0.94 | 0.43 | 1.38 | 0.15 |
| 3 | 320 | 30 | 92.95 | 3.04 | 1.56 | 0.33 | 0.37 | 0.45 | 1.16 | 0.13 |
| 5 | 300 | 30 | 92.98 | 3.13 | 1.33 | 0.29 | 0.34 | 0.51 | 1.3 | 0.13 |
| 7 | 280 | 30 | 93.2 | 3.1 | 0.95 | 0.23 | 0.3 | 0.54 | 1.55 | 0.14 |
| 15 | 340 | 15 | 93.47 | 2.38 | 0.46 | 0.17 | 0.55 | 0.59 | 2.13 | 0.26 |
| 17 | 320 | 15 | 93.69 | 2.15 | 0.34 | 0.1 | 0.4 | 0.72 | 2.34 | 0.26 |
| 19 | 300 | 15 | 93.73 | 2.1 | 0.29 | 0.08 | 0.35 | 0.71 | 2.46 | 0.29 |
| 21 | 280 | 15 | 93.63 | 2.09 | 0.27 | 0.08 | 0.33 | 0.77 | 2.54 | 0.28 | product stream in presence of a catalyst, the third product stream containing one or more alkyl monoaromatic compounds; and a second separator fluidly coupled to the hydrodearylation reactor and adapted to receive the third product stream and to produce a benzene-containing stream, a toluene-containing stream, a $C_8$-rich stream, and a bottoms $C_{9+}$ stream, the system adapted to combine the first product stream containing $C_9$ and $C_{10}$ compounds from the first separator and the bottoms $C_{9+}$ stream from the second separator.

2. The system of claim 1, further comprising:
a transalkylation/toluene disproportionation unit fluidly coupled to the second separator and adapted to receive the first product stream and one or more of the benzene-containing stream, the toluene-containing stream, and the bottoms $C_{9+}$ stream, and to produce alkyl monoaromatic compounds.

3. The system of claim 1, further comprising:
a para-xylene unit fluidly coupled to the second separator and adapted to receive the $C_8$-rich stream and to produce a para-xylene-rich stream.

4. The system of claim 1, further comprising:
a third separator fluidly coupled to the second separator and adapted to receive the benzene-containing stream and adapted to separate a benzene-enriched stream from toluene.

5. The system of claim 4, further comprising:
a fourth separator fluidly coupled to the second separator and the third separator, the fourth separator adapted to receive the toluene-containing stream from the second separator and adapted to receive toluene from the third separator to separate a toluene-enriched stream from $C_{8+}$ compounds.

6. The system of claim 5, further comprising:
a fifth separator fluidly coupled to the second separator and the fourth separator, the fifth separator adapted to receive the $C_8$-rich stream from the second separator and adapted to receive $C_{8+}$ compounds from the fourth separator to separate a $C_8$-enriched para-xylene production stream from $C_{9+}$ compounds.

7. The system of claim 1, wherein the feed stream is fluidly coupled to a xylene rerun column of an aromatic recovery process.

8. The system of claim 1, wherein the feed stream is supplied directly to the first separator from a xylene rerun column of an aromatic recovery process.

9. The system of claim 1, wherein a catalyst bed comprising catalyst in the hydrodearylation reactor is adapted to receive a portion of the hydrogen stream to quench the catalyst bed.

10. The system of claim 9, wherein the catalyst includes a support being at least one member of the group consisting of silica, alumina, titania, and combinations thereof, and further includes an acidic component being at least one member of the group consisting of amorphous silica-alumina, alumina, zeolite, and combinations thereof.

11. The system of claim 10, wherein the zeolite is one or more of or derived from FAU, *BEA, MOR, MFI, or MWW framework types.

12. The system of claim 9, wherein the catalyst includes an IUPAC Group 6-10 metal being at least one member of the group consisting of iron, cobalt, nickel, molybdenum, tungsten, and combinations thereof.

13. The system of claim 12, wherein an IUPAC Group 8-10 metal is 2 to 20 percent by weight of the catalyst and an IUPAC Group 6 metal is 1 to 25 percent by weight of the catalyst.

14. The system of claim 1, wherein conditions in the hydrodearylation reactor include an operating temperature in the range of about 200 to 450° C.

15. The system of claim 1, wherein conditions in the hydrodearylation reactor include an operating temperature in the range of about 250 to 450° C.

16. The system of claim 1, wherein conditions in the hydrodearylation reactor include an operating hydrogen partial pressure in the range of about 5 bar gauge to 100 bar gauge.

17. The system of claim 2, wherein the transalkylation/toluene disproportionation unit is adapted to increase the production of para-xylene.

18. The system of claim 9, wherein the catalyst in the catalyst bed does not comprise a metal.

19. The system of claim 9, wherein the catalyst in the catalyst bed does not comprise an IUPAC Group 6-10 metal.

20. The system of claim 9, wherein the catalyst bed comprises a catalyst support material and a binder operable to function as the catalyst without an added catalytic IUPAC Group 6-10 metal.

21. The system of claim 20, wherein the catalyst support material comprises a zeolitic material and the binder comprises alumina.

22. The system of claim 9, wherein an IUPAC Group 8-10 metal is 1 to 20 percent by weight of the catalyst, without an IUPAC Group 6 metal.

23. The system of claim 9, wherein an IUPAC Group 6 metal is 1 to 25 percent by weight of the catalyst, without an IUPAC Group 8-10 metal.

* * * * *